United States Patent
Lashmore

(10) Patent No.: US 6,991,459 B2
(45) Date of Patent: Jan. 31, 2006

(54) IMPACTOR AND PASTE FEEDER

(75) Inventor: David S. Lashmore, Lebanon, NH (US)

(73) Assignee: Innovative Dental Technologies, Inc., Lebanon, NH (US)

(*) Notice: Subject to any disclaimer, the term of this patent is extended or adjusted under 35 U.S.C. 154(b) by 0 days.

(21) Appl. No.: 10/625,476

(22) Filed: Jul. 22, 2003

(65) Prior Publication Data

US 2004/0131992 A1 Jul. 8, 2004

Related U.S. Application Data

(60) Provisional application No. 60/397,704, filed on Jul. 22, 2002.

(51) Int. Cl.
*A61C 3/08* (2006.01)

(52) U.S. Cl. .................. 433/83; 433/150; 173/112
(58) Field of Classification Search .......... 433/83, 433/118, 121, 150, 151; 173/112
See application file for complete search history.

(56) References Cited

U.S. PATENT DOCUMENTS

| | | | | |
|---|---|---|---|---|
| 3,280,459 A | * | 10/1966 | Walker et al. ............ | 433/82 |
| 3,623,244 A | * | 11/1971 | Smith .................... | 36/67 D |
| 3,638,314 A | * | 2/1972 | Lopez et al. ............ | 433/83 |
| 3,751,807 A | * | 8/1973 | Noll et al. .............. | 433/83 |
| 3,816,922 A | * | 6/1974 | Thiel et al. ............. | 433/83 |
| 3,921,044 A | * | 11/1975 | McShirley ............... | 318/114 |
| 5,711,866 A | | 1/1998 | Lashmore et al. ....... | 205/687 |
| 6,110,254 A | | 8/2000 | Johnson et al. ......... | 75/741 |

* cited by examiner

*Primary Examiner*—Cary E. O'Connor
(74) *Attorney, Agent, or Firm*—Borque & Assoc.

(57) ABSTRACT

An impactor for safely, efficiently, and effectively placing mercury-free dental restorations in a cavity of a patient's tooth, the impactor having a housing, anvil, hammer, solenoid or other transducer, end cap, source of restoration paste, and paste feeder tube for condensing mercury-free paste in the cavity. The impactor provides periodic impulses by activating the solenoid, causing the hammer to strike the anvil. The anvil is forced into contact with the paste, thereby condensing the paste into a high-density metal or other material suitable for dental restoration. (Also disclosed is a solenoid or other transducer having a "T" shaped hammer which strikes an anvil.) The solenoid or other transducer can be used to compact or strike any surface. The paste feeder may be incorporated into the impactor or alternatively be a separate hand operated device.

23 Claims, 3 Drawing Sheets

IMPACTOR AND PASTE FEEDER

CROSS REFERENCE TO RELATED APPLICATIONS

This application claims priority of U.S. Patent Application No. 60/397,704 filed on Jul. 22, 2002 and entitled Impact Condenser Slurry Feeder.

TECHNICAL FIELD OF THE INVENTION

The present invention relates to impactors and paste feeders in general. The present invention is described in the context of medical devices, particularly dental devices and practices.

DESCRIPTION OF THE RELATED ART

Several different types of dental restorative materials, primarily mercury-containing silver alloys (also known as silver amalgams), gold foils, and polymeric fillings, are currently placed in situ in the dental office. In contrast, ceramic and solid gold restorations require laboratory preparation.

Currently, the predominant dental restorative or filling material is mercury-containing silver alloy because of its relative convenience and longevity. Unfortunately, mercury-containing silver alloy contains approximately 50 percent weight mercury, which has serious negative health consequences for patients and dental practitioners and considerable negative environmental consequences.

When mercury-containing silver alloy fillings are administered, patients and dental practitioners are exposed to mercury. When mercury-containing alloy fillings are removed, the mercury vaporizes and the patients are again exposed to them. Further, the removal of these mercury containing alloy fillings are discarded as waste, and such removal causes serious environmental concerns as mercury waste enters public water treatment plants.

The long-term, serious negative health consequences of human exposure to dental mercury have been well documented. Dr. Haley Boyd, a foremost expert in this field, testified before the United States House of Representatives' Committee on Government Reform on Nov. 14, 2002 about the adverse health consequences of dental mercury.

Dental amalgams are the major contributor to the mercury body burden of American citizens. Dental amalgams release approximately 100 micrograms of mercury daily into the body. It is estimated that up to 0.7 tons of mercury waste in the air comes from dental office sources. In the United States, the dental industry uses over 30 metric tons of mercury annually; much or most of this mercury ends up in the environment, constituting 50 to 70 percent of the environmental load.

New regulations, such as stringent waste water regulations, regarding mercury-containing materials have been implemented in the United States, resulting in considerable expense to dental practitioners, consumers, and insurance companies. For example, the U.S. Environmental Protection Agency requirement to keep mercury-containing dental waste out of the water supply mandates waste mediation resulting in added costs and paperwork for dental practitioners.

Public wastewater treatment officials are calling on the dental industry to decrease the amount of mercury it introduces into wastewater treatment facilities. Since municipal wastewater treatment facilities are not designed to reduce mercury loadings to the environment, all mercury in the influent wastewater remains untreated and either settles in the sludge, which is either distributed on the land or incinerated, or passes through the wastewater treatment facilities into waterways.

When amalgam waste or mercury-laden sludge is incinerated, the mercury is released into the air, contributing to both the regional and the global mercury pool in the environment. Dental offices account for 40 percent of the mercury load. Human waste is the next greatest contributor of dental mercury entering into sewage waste treatment systems. Amalgam fillings are responsible for additional airborne releases through cremation. Dental amalgam is categorized as a hazardous waste, and landfill sites contaminated with mercury waste have been listed by the Environmental Protection Agency as Superfund Sites.

Mercury is now widely recognized as so dangerous that many institutions have restricted its use. Over the past few years, 15 states have passed legislation to eliminate the use of mercury in dental amalgams. Over 65 mercury product bills have been introduced in 24 states so far in 2003, and more mercury bills are expected to be passed in 2003 than in 2001 and 2002 combined. The Environmental Council of the States, an organization of top state government environmental officials across the United States, recently called for federal governmental support of "a binding international agreement on mercury to implement a comprehensive global mercury action plan to eliminate mercury release, uses, and mining." Existing amalgam alternatives carry significant risk; polymeric restorations contain organic chemicals whose long-term affects on the patient are not nearly as well documented as the effects of conventional amalgams, and these restorations tend to leak over time. Other mercury-free restorations such as gallium-based alloys, have presented problems, including those strength and bio-incompatibility, sufficiently critical to keep them from widespread commercial use. Ceramic restorations fail to hold up well in highly stressed situations and lack, as do polymeric composite restorations, the bactericidal properties of silver oxide present both in conventional amalgams and in this technology.

Extensive biocompatibility testing of the condensed silver restoration central to the subject technology, conducted as part of a NIDR-NIST 3-93-4 study, such as cell mutenicity tests and primate evaluations, showed that impact condensed silver combined with a dilute activation solution consisting of 2% tetrafluoroboric acid caused no tissue sensitivity that would preclude commercialization.

The advantages of mercury-containing silver amalgam are its high strength, the bactericidal properties of its silver oxide, its low cost, and its suitability for an efficient in-office restoration. While a pure silver restoration exists (U.S. Pat. No. 5,711,866 to Lashmore) which meets the present need for a mercury-free alternative to mercury-containing amalgam, the drawbacks of the prior art precluded its commercialization. The present invention addresses and resolves these drawbacks and thus meets the existing need for a mercury-free restoration that can be successfully commercialized and that provides in one system a combination of advantages (superior safety, efficiency, effectiveness, convenience, ease of proper installation, and lower cost) that is not provided by any one commercially available alternative.

SUMMARY OF THE INVENTION

The present invention consists of an impactor, a paste feeder, thermally sealed disposable cartridges containing restorative paste, and a power supply. The impactor uses a solenoid driven hammer to strike an anvil tip which contacts the restoration paste. The anvil tip welds the paste into a solid metal restoration in the cavity of a patient's tooth. The paste feeder can either be incorporated into the handle of the impactor or it can be part of a separate instrument. The cartridges contain a restoration paste of pure silver and dilutes 2% tetrafluoroboric acid ($HBF_4$).

The purpose of this invention is to provide a safer, more precise, more effective, more efficient system for the placement of an in situ dental restoration that is free of mercury, gallium, and indium and that is inherently safer, better performing, longer lasting, easier to install properly, and more convenient than a silver-mercury restoration.

The present invention also provides a means of reducing the amount of mercury waste entering wastewater treatment systems, reducing waste water treatment requirements for dental practitioners, and reducing the amount of mercury waste released into the environment.

The present invention solves at least three problems in the prior art: (1) the time required to install the restoration, (2) the low density of the restoration when installed by hand instruments, and (3) the need to remove the activating solution during the condensation. The present invention solves these three problems by offering a means for automatically and rapidly injecting a paste of silver and dilute 2% tetrafluoroboric acid into the cavity of a patient's tooth and rapidly impact condensing the silver paste into a highly dense in situ restoration. With alternative embodiments of the subject impactor, gold foil or gold alloy powder is impact condensed into a gold restoration. The high density of the materials and short time to impact condense them solves the major problems in the prior art.

The present invention also has applications beyond that of dental restoration. For example, the impactor has a solenoid that can be scaled up and applied to the pressing of powders in larger powder metallurgy dies to mass-produce parts. The advantage of compacting powders with a repetitive impacting solenoid system is that very high impulse loading is obtained with relatively low static loads, resulting in parts of much higher density and lower part expansion in the die.

In an alternative embodiment of the present invention, the impactor is battery-powered making it ideal for veterinary and military applications and for general field use.

BRIEF DESCRIPTION OF THE DRAWINGS

These and other features and advantages of the present invention will be better understood by reading the following detailed description, drawings, and claims, wherein:

DETAILED DESCRIPTION

U.S. Pat. No. 5,711,866 to Lashmore, which is hereby incorporated by reference, is a process for providing a mercury-free in situ dental restoration. The process uses hand pressure to condense paste of silver or silver alloys and an activation solution of dilute 2% tetrafluoroboric acid. The tetrafluoroboric acid is a flux to remove the oxide during condensation, enabling the silver particles to cold weld to each other. The process offers a low cost, superior alternative to mercury-containing restorations. The principal drawbacks are the time required to install the restoration, the low density of the restoration when installed by hand instruments, and the need to remove the activation solution during the condensation.

Figure 1:
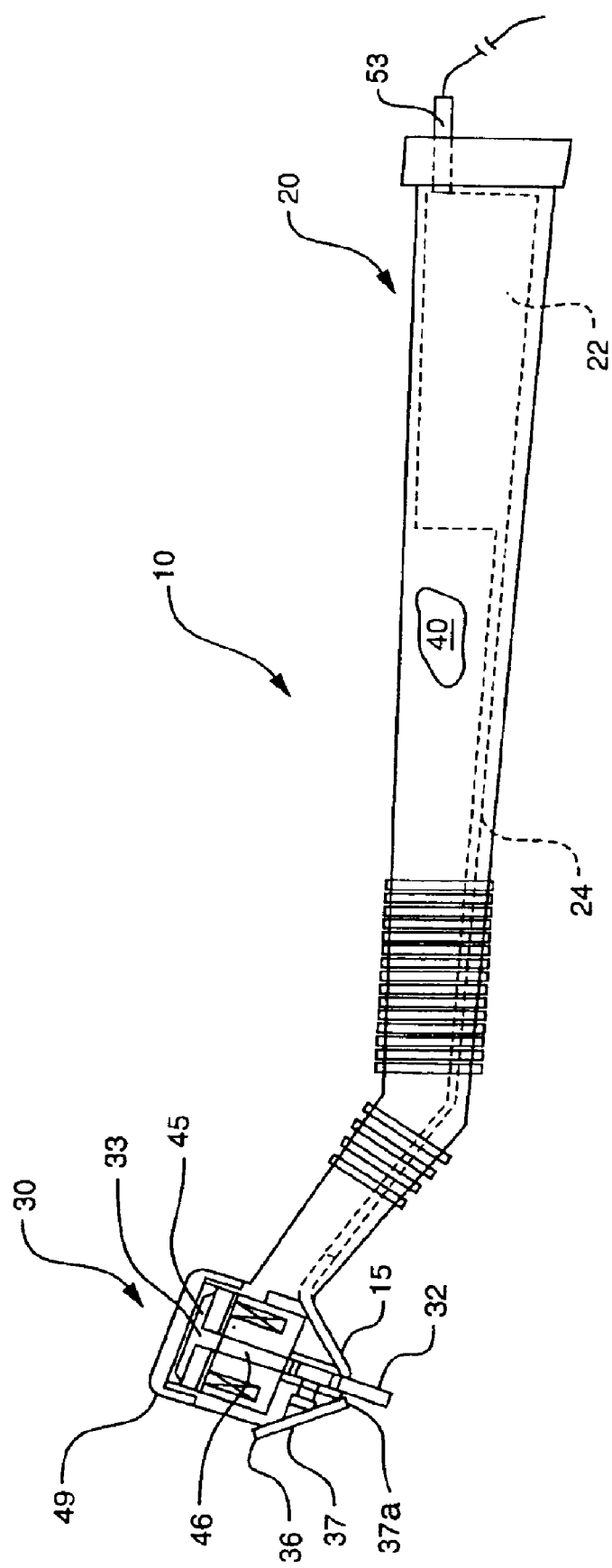
FIG. 1 is a side view of an impactor having a head and a handle with a cross-sectional view through the head according to the present invention.

The present invention addresses and resolves these drawbacks. An impactor 10 according to the present invention is shown in FIG. 1. The impactor 10 has a handle 20 and a head 30. The handle 20 has a cavity 40 for receiving a removable paste cartridge 22. The paste cartridge 22 holds paste and is either disposable or reusable. The paste cartridge 22 is pressurized as described below. In the disposable embodiment, the paste cartridge 22 is preferably heat sealed for long-term storage, and both ends of the paste cartridge 22 are cut open prior to insertion into the cavity 40 of the handle 20 or other paste feeding system.

The paste preferably has a combination of silver and activation solution. In the preferred embodiment, the activation solution is dilute 2% tetrafluoroboric ($HBF_4$) acid. Alternatively, the paste has a silver alloy or gold alloy. Gold foil combined with the activation solution may be used in lieu of the paste but would require hand placement. The resultant silver, gold-alloy powder, or gold foil is condensed in the cavity of a patient's tooth. This technology is designed to repair the damage caused by decay or corrosion of existing fillings.

The paste is fed into the cavity of the patient's tooth with either a pneumatic or a mechanical feeder. In the preferred embodiment, a paste feeder tube 24 is used to transport the paste from the paste cartridge 22 to a paste dispensing tip 15 is located adjacent to an anvil 32 which extends from the head 30. The paste feeder tube 24 may extend along, in, or be integral to, the handle 20. When the paste feeder tube 24 extends along the handle 20 and the head 30, grooves (not shown) on the exterior of the handle are used to receive and secure the paste feeder tube 24 thereto. Clips (not shown) could be used in lieu of the grooves.

When assembled, the paste cartridge 22 and paste feeder tube 24 are sealed creating a pressurized capsule. The paste is forced from the paste cartridge 22 through the paste feeder tube 24 to the paste dispensing tip 15 via a pneumatic supply source (not shown). The supply source, known to those having ordinary skill in the art, is operatively attached to the paste cartridge 22 and/or paste feeder tube 24 via a pneumatic control valve 53 or other similar means. The pneumatic control valve 53 controls the flow of air in the paste feeder tube 24. The dental practitioner uses the pneumatic control valve 53 to control the air pressure from the supply source to urge or force the paste from the paste cartridge 22 to the anvil tip 32a and ultimately into the cavity of the patient's tooth. This valve 53 is preferably located on the handle 20 of the device. The valve 53 could also be a foot activated valve.

In a first alternative embodiment, the paste feeder tube 24 is operatively connected to an external source of paste material instead of the paste cartridge 22.

Figure 4:
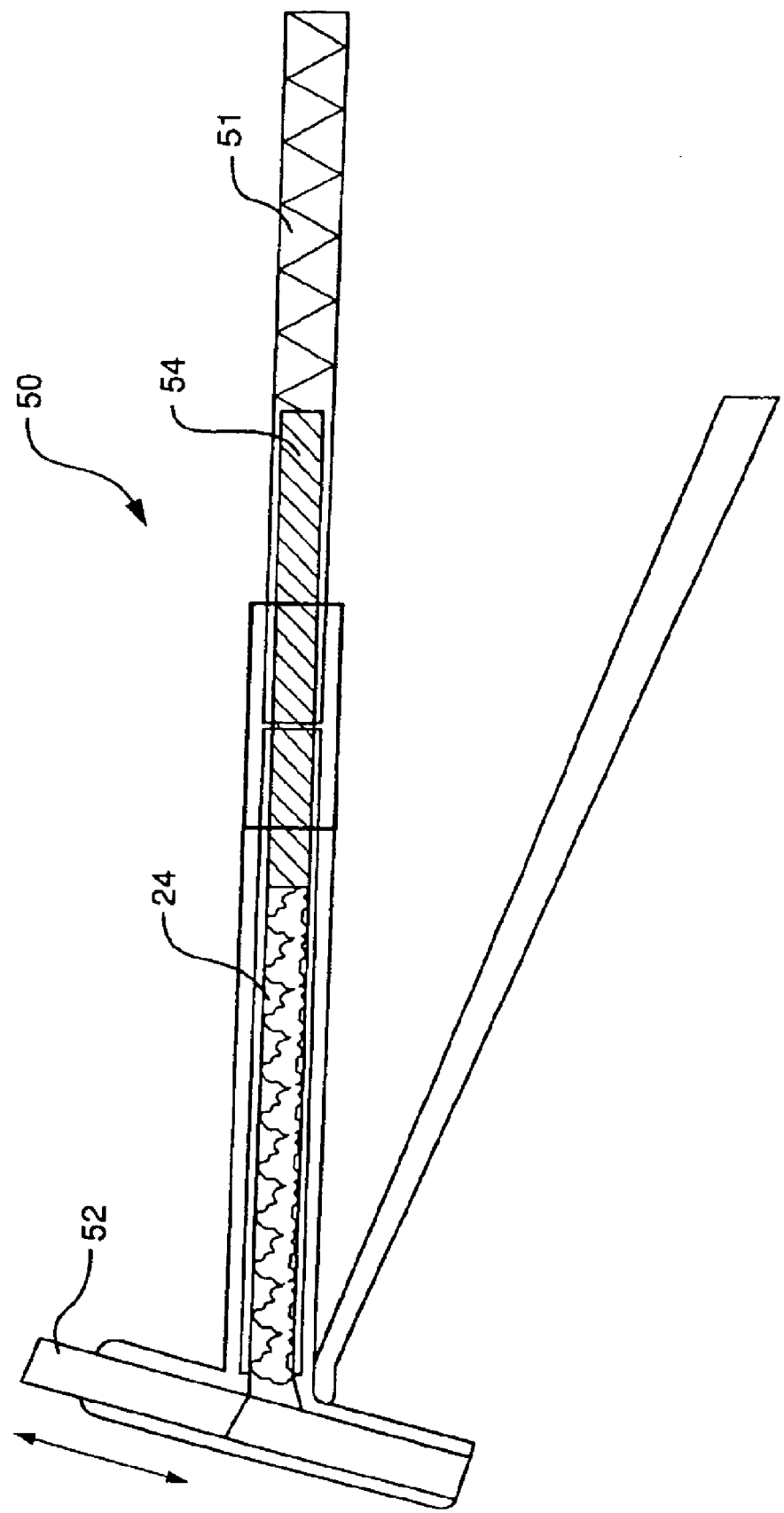
FIG. 4 is a side view of an alternative embodiment of a paste feeder.

In a second alternative embodiment, a mechanical paste feeder 50, FIG. 4, is used to allow preliminary condensation of the paste prior to contact by the anvil 32. A spring 51 pushed a plunger 54, which forces a certain amount of the paste determined by the operator into the paste feeder tube 24. An ejector pin 52 forces the paste in the feeder 50 into the cavity of the patient's tooth and applies pressure onto the dispensed paste until the operator starts the condensation process. The mechanical paste feeder 50 delivers the same amount of material each time it is activated, pre-compacts the paste, and eliminates the need for a pneumatic supply source.

In a third embodiment, a constant displacement apparatus similar to the mechanical feeder of FIG. 4 can be substituted for the spring 51 and the plunger 54. Each time a feed handle of the constant displacement apparatus is squeezed, the plunger 54 moves the paste the same incremental distance.

The head 30 has a housing 35 made of a corrosion-resistant material, such as nonmagnetic stainless steel, preferably 316 stainless steel, or a polymer such as Teflon®, nylon, or Vespel®. The housing 35, FIG. 2, has a diameter of approximately 0.5 of an inch, and a height of approximately 0.75 of an inch although such dimensions are not a limitation to the present invention. The housing 35 has an opening 42 for receiving the anvil 32 and a threaded hole 59 for receiving a set screw 41. The set screw 41 is used to hold the anvil 32 in place during use and to release the anvil 32 during non-use. One of the ends of the set screw 41 almost contacts the anvil 32 between stops 58. The anvil 32 is allowed to move vertically while the set screw 41 and the stops 58 limit the vertical movement. There are other devices for holding and releasing the anvil 32, such as a spring clip (not shown), which can be substituted for the set screw 41. The set screw 41 or spring clip allows efficient removal of the anvil 32 and other parts of the impactor 10 for cleaning and sterilization.

Figure 2:
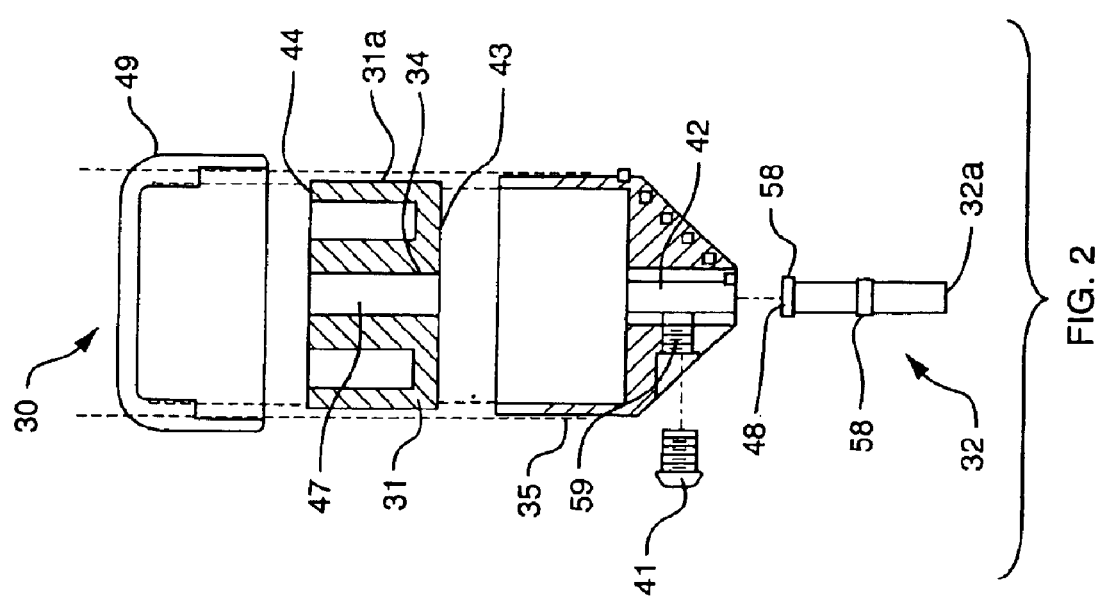
FIG. 2, an enlarged, exploded view of the head of the impactor shown in FIG. 1 shows a solenoid, hammer, anvil, and end cap.

The anvil 32, FIG. 2, is preferably made of Inconel®, 316 stainless steel, or a similar material. The anvil 32 is replaceable. The anvil 32 extends from a bottom base 43 of a solenoid 31, protrudes out from the housing 35, and contacts the paste when in use. The anvil 32 is at an angle from the handle 20. In the preferred embodiments, the angle between the long portion of the handle 20 and the anvil 32 is between 90 to 105 degrees; however, the angle may be varied depending on the dimensions of the cavity of the patient's tooth, the operator's preference, and the filling requirements.

The anvil tip 32a may be flat, serrated, rounded, concave, or shaped in any other configuration desired by the dental practitioner to access difficult to reach portions of the cavity. The anvil tip 32a directly contacts the paste or filling material during impaction. The anvil tip 32a may have a smaller diameter than a remaining portion of the anvil 32 and may thus form a small ledge near a bottom of the anvil 32, which acts as a pump to help move the paste to the anvil tip 32a.

The solenoid 31 is operatively mounted between an end cap 49 and the housing 35. In one embodiment, the solenoid 31 is bonded into the housing 35. The solenoid 31 generates impact energy which is small but powerful. Alternatively, the impact energy is generated by a piezoelectric transducer, a magnetostrictive transducer, an electrostatic transducer, a small electric motor driving a cam, or a pneumatic transducer. Other solenoids that are known by those having ordinary skill in the art include full conical, tapered plunger, and cylindrical magnet types. Herbert C. Roters, *Electromagnetic Devices*, 1$^{st}$ ed., John Wiley and Sons Inc., New York, 1941, p. 228, which is hereby incorporated by reference, describes some of these devices. The static force is about 8 pounds and the impact force is about 16 pounds. The frequency varies from 5 hertz (Hz) to 20 Hz preferably around 8 Hz to 10 Hz.

In the preferred embodiment, a solenoid control unit (not shown) is operatively connected to the solenoid 31. The solenoid control unit provides current pulses for controlling the solenoid 31.

A constant current waveform is used to drive the solenoid 31. The waveform frequency varies from approximately 5 Hz to approximately 20 Hz. In the preferred embodiment, the waveform frequency is approximately 10 Hz. A pulsed current is ideally timed to turn on when a hammer 33 is furthest from the top surface 44 of the solenoid 31; however, a free running waveform is also possible. This waveform is preferably a square wave; however, the waveform can be sinusoid. A 110V ac driven system and battery driven system can be substituted for the constant current waveform.

The solenoid 31 includes a stator 31a. The stator 31a is made from a soft magnetic material such as a silicon iron alloy. The stator 31a has a coil pocket with a preformed copper coil capable of supporting approximately 200 amp turns. Alternately, the stator 31a may be made of an encapsulated soft magnetic material such as Somalloy 500 (from Haganous in Sweden). The preformed copper coil is injection molded and sealed so that the entire unit can be taken apart and sterilized.

Figure 3:
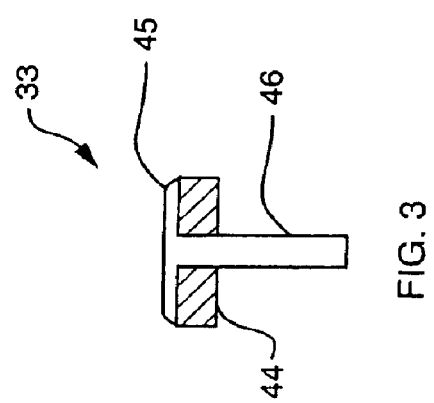
FIG. 3 is a side view of the hammer of the impactor.

The hammer 33 includes portions 45 and 46 made from a hardened steel, steel, or preferably Inconel®. Bonded to the horizontal portion 45 of the hammer 33 is a top surface 44, the top surface 44 is made of a soft magnetic material such as 2.5% SiFe, silicon iron alloys, phosphorus-containing iron alloy, nickel, chromium, iron alloy, iron polymer composite, iron-inorganic coated composites, iron phosphorus, or iron aluminum alloy. The hammer 33 is "T" shaped in the preferred embodiment as shown in FIG. 3. The hammer 33 has a horizontal portion 45 and a vertical portion 46. In the preferred embodiment, the horizontal portion 45 is an Inconel® disk integral with vertical portion 46 and machined out of a single piece of Inconel® to which the soft magnetic disk is bonded.

A bottom surface of the horizontal portion 45 is above the top surface 44 of the solenoid 31, shown in FIG. 2. The solenoid 31 has a slot 47 and an inner surface of the slot 47 has a sleeve bearing 34 thereon. The sleeve bearing 34 of the slot 47 receives the vertical portion 46 of the hammer 33. The vertical portion 46 extends beyond the bottom surface 43 of the solenoid 31 and is used to strike or contact the anvil 32. The vertical portion 46 of the hammer 33 slides up and down in the sleeve bearing 34 of the slot 47. The sleeve bearing 34 can be made of any suitable material, such as a phosphorous bronze or polytetraflouethylene (PTFE or Teflon®). The vertical portion 46 of the hammer 33 is in contact with a top surface 48 of the anvil 32.

The hammer 33 is forced downward by a magnetic attraction created by the solenoid 31. When the hammer 33 is forced downward by the solenoid 31, the vertical portion 46 of the hammer 33 strikes the anvil 32, thereby driving the anvil 32 into the paste. The solenoid 31 has a static force of about 8 pounds at contact. The hammer 33 moves upward because of the elastic rebound following the collision with the anvil 32. The rebound from this impact serves as a return spring.

When the hammer 33 moves up and down in the sleeve bearing 34 of the slot 47, the hammer 33 moves a vertical distance between approximately 0.010 to 0.040 of an inch. In the preferred embodiment, the hammer 33 moves a vertical distance of approximately 0.020 of an inch. The hammer 33 is restricted in its downward movement by the top surface 48 of the anvil 32 and in its upward movement by the end cap 49. The hammer 33 drives the anvil 32, thereby providing impulse loading to a silver powder in the paste, which was previously fed through the paste feeder tube 24 to the cavity in the patient's tooth, causing it to cold weld together into a dense filling.

The end cap 49 is removably mounted to the housing 35. In the preferred embodiment, the end cap 49 is screwed onto the housing 35. The end cap 49 and the housing 35 have mating threads. In an alternative embodiment, the end cap 49 is fastened to the housing 35 with spring clips (not shown).

A power supply (not shown) is used to give the dental practitioner the ability to independently control the force and the frequency of the impact of the anvil 32 by providing a series of current (voltage) pulses that periodically turn the electromagnet of the solenoid 31 on and off.

The power supply is a free running square wave current source or waveform synchronized with the position of the hammer 31, thereby turning on the current when the hammer 31 is furthest from the top surface 44 of the solenoid 31. The frequency ranges from 5 Hz to 20 Hz, preferably around 10 Hz. The current waveform is approximately a square-wave and is achieved by rapidly switching a constant current power supply at the desired frequency. Both the magnitude of the current and the frequency can be varied. It is possible to drive the solenoid 31 with a constant voltage waveform.

The frequency of this current waveform varies from approximately 5 Hz to approximately 20 Hz. The most desirable frequency is approximately 10 Hz, though this device can operate at frequencies up to 1000 Hz. A 110V ac driven system or a battery driven system can be used to drive the solenoid 31.

A suction tube 37 has a first end 37a operatively attached to the housing 35 and a second end operatively attached to a vacuum system 36. The vacuum system 36 is preferably a continuously operating system. The suction tube 37 has a hollow core for removing liquids, semi-liquids, solids, and foreign matter from the patient's mouth. The first end 37a of the suction tube 37 is proximate the anvil tip 32a of the anvil 32. The vacuum system 36 creates suction or a vacuum for removing the activation solution of the paste once the silver is condensed.

A separate vacuum system (not shown) known to those having ordinary skill in the art can be used for removing the patient's saliva, paste, particles from the removed filling, and other matter from the patient's mouth.

The external parts of the impactor 10 are stainless steel or as otherwise indicated herein, and the internal parts are removable for sterilization.

In an alternative embodiment, the impactor 10 is also used for cold welding, including solder bonding with pure silver or pure gold, thereby eliminating lead from the workplace and the undesirable side effects of tin, such as whisker formation and inter-metallic development.

In another alternative embodiment, the impactor 10 is scaled up to approximately 15 inches or greater in diameter and used to compact metal powders in a powder metallurgy die. The effective stress under the anvil 32 is greater than a factor of two and greater than the static stress under the solenoid 31, thereby magnifying the compaction and increasing density. For example, if the solenoid 31 is increased to 20 inches in diameter, the solenoid 31 will produce a compaction stress of over 14 tons. This compaction could then be repeated as often as required to obtain the required density.

The impactor 10 is assembled by placing the anvil 32 in the opening 42 of the housing 35. The anvil 32 is secured to the housing 35 via the set screw 41. One of the ends of the set screw 41 contacts the anvil 32 between the stops 58. The anvil 32 is allowed to move vertically but the set screw 41 and the stops 58 limit the vertical movement. The solenoid 31 is placed on the anvil 32 so that the slot 47 receives top portion 48 of the anvil 32. The vertical portion 46 of the hammer 33 is placed through the slot 47 having the sleeve bearing 34 and rests on the top portion 48 of the anvil 32. The end cap 49 is secured to the housing 35.

To operate the impactor 10, one or more of the ends of the paste cartridge 22 are cut, and the paste cartridge 22 is placed into the cavity 40 of the handle 20. The solenoid 31 is periodically activated via the power unit or pneumatic control unit. When the solenoid 31 is activated, the hammer 33 is forced downward by a magnetic attraction created by the solenoid 31. When the hammer 33 is forced downward by the solenoid 31, the vertical portion 46 of the hammer 33 strikes the anvil 32, thereby driving the anvil 32 into the paste. The periodic impulse causes a high contact stress sufficient to condense the layer of metal paste to a high-density metal suitable for dental restorations. After the collision between the hammer 33 and the anvil 32, the hammer 33 moves upward because of the elastic rebound. The rebound from this impact serves as a return spring. Layers of paste are impacted until the cavity in the patient's tooth is filled.

Modifications and substitutions by one of ordinary skill in the art are considered to be within the scope of the present invention.

Concentrations range from 0.5% to about 10%, an optimal concentration is about 2%. Particle sizes range from about 5 microns to about 50 microns. Both the silver and gold powders or foils are well annealed.

What is claimed is:

1. An impactor, for producing an in situ dental restoration, comprising:
   a handle connected to a head;
   said head including a housing, an end cap, and a solenoid disposed between said housing and said end cap, said solenoid for driving a hammer in a downward direction into an anvil upon activation of said solenoid;
   said anvil having an anvil tip for impacting paste in a cavity of a patient's tooth when driven downward;
   a source of dental restoration paste; and
   a paste feeder tube, coupled to said source of dental restoration paste, for directing the dental restoration paste from the source of dental restoration paste to a location proximate the anvil tip.

2. The impactor for producing an in situ dental restoration according to claim 1, wherein said source of dental restoration paste includes a disposable paste cartridge.

3. The impactor for producing an in situ dental restoration according to claim 2, further including a paste feeder, for forcing the paste from the paste cartridge through the paste feeder tube to proximate the anvil tip.

4. The impactor for producing an in situ dental restoration according to claim 3, wherein the paste feeder for forcing the paste from the paste cartridge through the paste feeder tube to the anvil tip is a pneumatic paste feeder.

5. The impactor for producing an in situ dental restoration according to claim 3, wherein the paste feeder for forcing the paste from the paste cartridge through the paste feeder tube to the anvil tip is a mechanical paste feeder.

6. The impactor for producing an in situ dental restoration according to claim 5, wherein the mechanical feeder includes a piston for displacing a controlled amount of paste to the cavity of the patient's tooth.

7. The impactor for producing an in situ dental restoration according to claim 2, wherein said anvil is disposed at an angle relative to a long portion of said handle, and wherein said angle is between approximately 90 degrees and approximately 105 degrees.

8. The impactor for producing an in situ dental restoration according to claim 1, wherein the hammer is "T" shaped, said hammer having a horizontal portion and a vertical portion, said horizontal portion extending above a top surface of the solenoid and below the end cap, and said vertical portion extending through a slot in the solenoid and in contact with the anvil.

9. The impactor for producing an in situ dental restoration according to claim 8, further including a bearing sleeve on an inside surface of the slot, for receiving the vertical portion of the hammer.

10. The impactor for producing an in situ dental restoration according to claim 9, further including a solenoid power supply for providing a pulse current to the solenoid, and wherein said solenoid receives the pulse current when the horizontal portion of the hammer is at its furthest distance from the top surface of the solenoid, thereby driving the vertical portion of the hammer downward into the anvil.

11. The impactor for producing an in situ dental restoration according to claim 10, wherein the hammer rebounds upward from the impact with the anvil.

12. The impactor for producing an in situ dental restoration according to claim 11, wherein the top surface of the solenoid stops the hammer in its downward movement and the end cap stops the hammer in its upward movement.

13. The impactor for producing an in situ dental restoration according to claim 8, wherein the horizontal portion of said hammer is made from a hard steel and having a lower surface to which is bonded a disc made of a soft magnetic material.

14. The impactor for producing an in situ dental restoration according to claim 1, wherein the anvil tip is flat.

15. The impactor for producing an in situ dental restoration according to claim 1, wherein the anvil tip is serrated.

16. The impactor for producing an in situ dental restoration according to claim 1, wherein the anvil extends from a bottom surface of the solenoid, and wherein said anvil is made from 2.5% silicon soft magnetic annealed iron.

17. The impactor for producing an in situ dental restoration according to claim 1, wherein the paste comprises a hardening agent and a material selected from the group consisting of silver, silver alloys, gold, and gold alloy powder in paste form to which is added 2% $HBF_4$.

18. The impactor for producing an in situ dental restoration according to claim 17, further including a vacuum system for removing liquids, semi-liquids, and solids from the cavity.

19. The impactor of claim 1 wherein the solenoid is replaced by a transducer selected from the group consisting of an electrostatic transducer, a magnetostrictive transducer, a pneumatic transducer an electric motor and an hydraulic drive.

20. A solenoid driven impactor, comprising:
a solenoid disposed in a housing having a top, said solenoid for driving a hammer in a downward direction into an anvil upon activation of said solenoid, said anvil having an anvil tip for impacting a surface;
a "T" shaped hammer, said hammer having a horizontal portion and a vertical portion, said horizontal portion disposed above a top surface of said solenoid, and said vertical portion extending through a slot in the solenoid and in contact with said anvil;
a solenoid power supply, for providing a pulse current to activate the solenoid, and wherein said solenoid receives the pulse current when the horizontal portion of the hammer is at its furthest distance from the top surface of the solenoid, thereby driving the vertical portion of the hammer downward into the anvil; and
wherein the hammer rebounds upward from the impact with the anvil, and wherein the top surface of the solenoid stops the hammer in its downward movement and the housing top stops the hammer in its upward movement.

21. A transducer driven impactor, comprising:
a transducer, disposed in a housing having a top, said transducer for driving a hammer in a downward direction into an anvil upon activation of said transducer, said anvil having an anvil tip for impacting a surface;
a "T" shaped hammer, said hammer having a horizontal portion and a vertical portion, said horizontal portion disposed above a top surface of said transducer, and said vertical portion extending through a slot in the transducer and in contact with said anvil;
a transducer power supply, for providing a pulse current to activate the transducer, and wherein said transducer receives the pulse current when the horizontal portion of the hammer is at its furthest distance from the top surface of the transducer, thereby driving the vertical portion of the hammer downward into the anvil; and
wherein the hammer rebounds upward from the impact with the anvil, and wherein the top surface of the transducer stops the hammer in its downward movement and the housing top stops the hammer in its upward movement.

22. An impactor for producing an in situ dental restoration, comprising:
a handle connected to a head;
said head including a housing, an end cap, and a transducer disposed between said housing and said end cap, said transducer for driving a hammer in a downward direction into an anvil upon activation of said transducer;
said anvil having an anvil tip for impacting paste in a cavity of a patient's tooth when driven downward;
a source of dental restoration paste; and
a paste feeder, coupled to said source of dental restoration paste, for directing the dental restoration paste from the source of dental restoration paste to a location proximate said in a cavity of a patient's tooth.

23. The impactor for producing an in situ dental restoration according to claim 22, wherein the transducer is selected from the group consisting of an electrostatic transducer, an electric motor, and a hydraulic drive.

* * * * *